United States Patent
Lu et al.

(10) Patent No.: US 9,370,381 B2
(45) Date of Patent: Jun. 21, 2016

(54) BONE CONNECTION MATERIAL

(71) Applicants: Luke Lu, South Pasadena, CA (US);
Toshihiro Tokizawa, Tokyo (JP);
Kuan-Yu Lu, Taipei (TW); I-Ching Lu,
Taipei (TW)

(72) Inventors: Luke Lu, South Pasadena, CA (US);
Toshihiro Tokizawa, Tokyo (JP);
Kuan-Yu Lu, Taipei (TW); I-Ching Lu,
Taipei (TW)

( * ) Notice: Subject to any disclaimer, the term of this patent is extended or adjusted under 35 U.S.C. 154(b) by 304 days.

(21) Appl. No.: 14/164,258

(22) Filed: Jan. 27, 2014

(65) Prior Publication Data

US 2015/0209484 A1 Jul. 30, 2015

(51) Int. Cl.

| | |
|---|---|
| *A61B 17/68* | (2006.01) |
| *A61L 31/08* | (2006.01) |
| *A61B 17/86* | (2006.01) |
| *A61L 31/04* | (2006.01) |
| *A61L 31/02* | (2006.01) |
| *A61L 31/10* | (2006.01) |
| *A61L 31/16* | (2006.01) |
| *A61F 2/28* | (2006.01) |
| *A61B 17/70* | (2006.01) |
| *A61B 17/80* | (2006.01) |

(52) U.S. Cl.
CPC ............ *A61B 17/68* (2013.01); *A61B 17/7002* (2013.01); *A61B 17/80* (2013.01); *A61B 17/866* (2013.01); *A61B 17/869* (2013.01); *A61F 2/28* (2013.01); *A61L 31/026* (2013.01); *A61L 31/028* (2013.01); *A61L 31/044* (2013.01); *A61L 31/086* (2013.01); *A61L 31/10* (2013.01); *A61L 31/16* (2013.01); *A61L 2430/02* (2013.01)

(58) Field of Classification Search
CPC .. A61B 17/7002; A61B 17/80; A61B 17/866; A61B 17/68; A61F 2/28; A61L 31/026; A61L 31/028; A61L 31/044; A61L 31/086; A61L 31/16; A61L 2430/02
See application file for complete search history.

(56) References Cited

U.S. PATENT DOCUMENTS

| | | | |
|---|---|---|---|
| 5,711,960 A * | 1/1998 | Shikinami | A61F 2/0063 424/425 |
| 2005/0136764 A1* | 6/2005 | Sherman | A61B 17/7059 442/103 |

* cited by examiner

*Primary Examiner* — Larry E Waggle, Jr.
(74) *Attorney, Agent, or Firm* — Leong C. Lei

(57) ABSTRACT

The present invention provides a bone connection material that includes an internal layer. The internal layer is formed by braiding a plurality of filaments. The internal layer that is formed by braiding filaments is resistant to lateral shearing forces and may provide flexibility so as to achieve wide applications. Further, the present invention overcomes the drawback of the conventionally used metallic materials that are rigid and inelastic and also overcomes the problem of polylactic acid material of being brittle. Thus, the bone formed according to the present invention is close to a natural bone and is more suitable for uses in portions where frequent movements are made and scaffolds of stem cells.

4 Claims, 13 Drawing Sheets

BONE CONNECTION MATERIAL

TECHNICAL FIELD OF THE INVENTION

The present invention generally relates to a bone connection material and a manufacturing method thereof, and more particularly to a bone connection material that is made by braiding fiber filaments and resin matrix.

DESCRIPTION OF THE PRIOR ART

In the surgical operations, bone screws and bone plates are commonly used as a connection member for connecting teeth bone, cranial bones, facial and limb fractures. When the patient's body makes movements, the nail screws and nail bones that serve s the connection members may induce stresses, so that materials, such as titanium and steel, are commonly used to make bone screws and bone plates.

Further, when the bone screws and bone plates that are made of titanium or steel are placed in the bone connection of a patient, due to the natures of the materials that are rigid and inelastic, it often results in obstruction to the movements of the joint. Further, a bone connection material screw made of polylactic acid and hydroxylapatite is also available, but it has a disadvantage of being brittle in nature so that it may get cracking when subjected to an external force. It only works as an ancillary connection material for positioning purpose and is not fit for portions where frequent movements are made.

In light of the above, the present invention aims to provide a solution that overcomes the drawbacks.

SUMMARY OF THE INVENTION

In view of the above-discussed problems, the present invention aims to provide a bone connection material that comprises an internal layer. The internal layer is formed by braiding a plurality of filaments. The internal layer that is formed by braiding filaments is resistant to lateral shearing forces and may provide flexibility so as to achieve wide applications, and is fitter for portions where frequency movements are made than the conventionally used material of steel, and in addition, is not so inclined to be rejected by human body as the conventionally used metallic material.

Further, the present invention may further comprise a covering layer. The covering layer is arranged to enclose the filaments of the internal layer.

Preferably, the covering layer is made of a thermoplastic resin or a thermosetting resin or any biocompatible resin to improve elasticity.

Preferably, the covering layer further comprises collagen, screws made of polylactic acid, or hydroxylapatite. Interaction induced between these materials and inner tissues may help to increase the speed of growth and restoration of bones.

Preferably, the filaments are bioactive glass fibers, bioactive materials, or bioinert glass fibers, or bioinert materials, which are selected according to the site and property of the bone connection material used and can be manufactured to show a desired outer configuration so as to provide far superior capability of promoting bone healing to the prior art.

Preferably, the inner layer is made in the form of a bone screw, a bone plate, or bone rod, to suit the need of use of the contemporary technology.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

The embodiments of the present invention are a bone connection material. To make those skilled in the art to undoubtedly understand the embodiments, the structures of the bone connection materials will be described first. The materials and types of filaments that are used in the embodiments will then be discussed.

Figure 1:
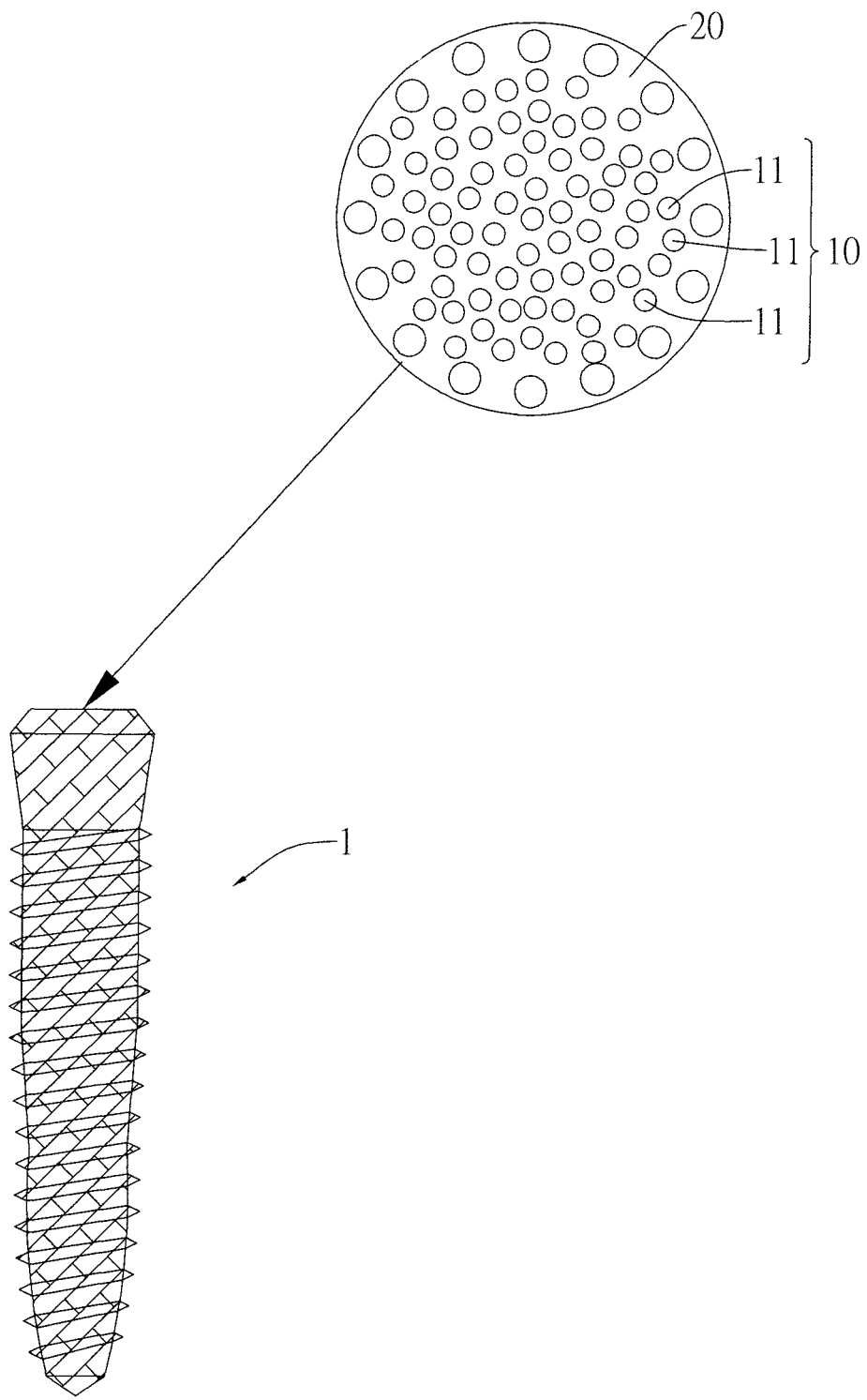
FIG. 1 shows a side elevational view and an enlarged top view of an embodiment of the present invention that is made by being braided as a screw.

Referring to FIG. 1, a bone connection material 1 according to an embodiment of the present invention is show, which comprises an internal layer 10 and a covering layer 20. The internal layer 10 is made by braiding a plurality of filaments 11 to show in a predetermined form that corresponds to a desired bone connection material. The covering layer 20 encloses the filaments 11 of the internal layer 10. The plurality of filaments 11, after being braided properly, results in a combination of the strength of all the filaments to thereby provide a material that is resistant to fracture and shows flexibility, making it suitable for connection of bones or serving as a framework of stem cells. In an actual operation, it is possible to solely form the internal layer 10 through braiding the filaments and the internal layer 10 is thus made in the form of a bone connection material.

Figure 8:
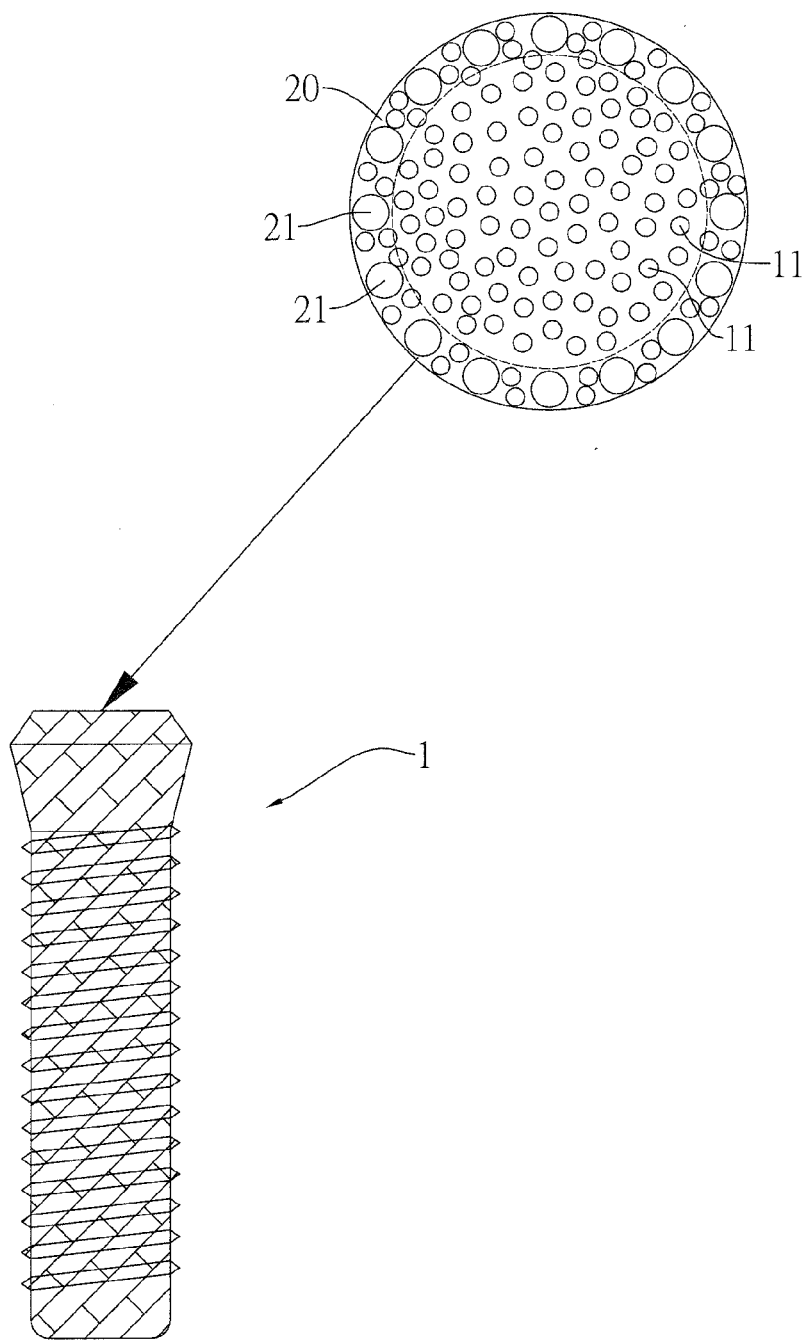
FIG. 8 shows an embodiment of the present invention that is made by being braided as a screw and a top view of the screw.

Further, an arrangement of the covering layer 20 may be additionally included so as to make the application of the bone connection material wide. The covering layer 20 is made of a thermoplastic resin, a thermosetting resin, biocompatible polymer or a biodegradable resin and matrix collagen, hydroxylapatite (HA), or may further include other additives 21, as shown in FIG. 8, such as collagen, hydroxylapatite (HA), or tricalcium phosphate (TCP). HA is a major constituent of human bone tissues and once implanted in human bodies, may release calcium and phosphorus that may be absorbed by body tissues to grow new tissues. Generally, the human body will itself generate HA or related or similar elements for proceeding with reconstruction of bones, but the time it may take is dependent on the individual body. The covering layer provided by the present invention is provided to contain such bone reconstruction materials so as to be used for body reconstruction and to provide an effect of accelerated restoration.

Further, the filaments 11 can be bioactive glass fibers, ceramic fiber materials, bioactive materials, or bioinert glass fiber materials, which can be used and arranged corresponding to the needs of the actual situations.

Figure 2:
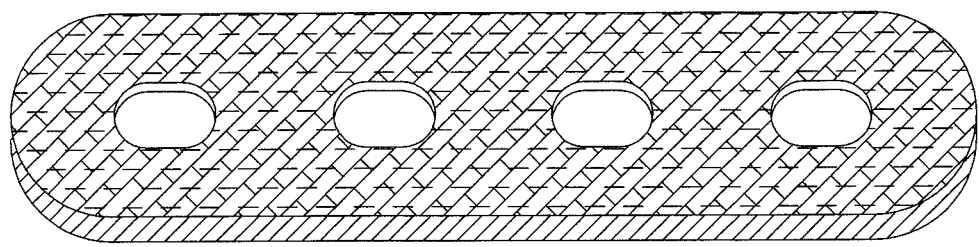
FIG. 2 shows a perspective view of an embodiment of the present invention that is made by being braided as a bone connection plate.
Figure 3:
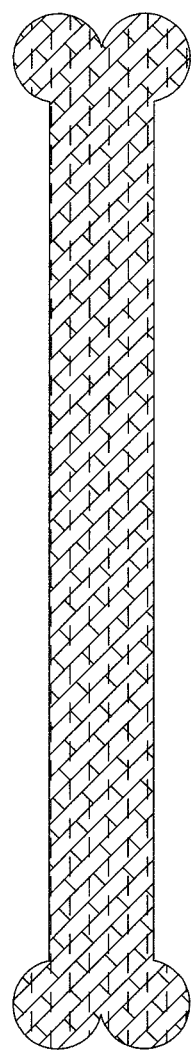
FIG. 3 shows a plan view of an embodiment of the present invention that is made by being braided as a bone or pipe bone shape.
Figure 4:
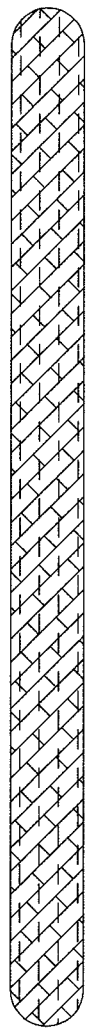
FIG. 4 shows a plan view of an embodiment of the present invention that is made by being braided as a bar, rod or pipe shape.
Figure 5:
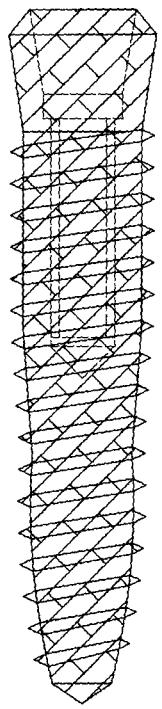
FIG. 5 shows a side elevational view of an embodiment of the present invention that is made by being braided as a screw having an internal thread.
Figure 6:
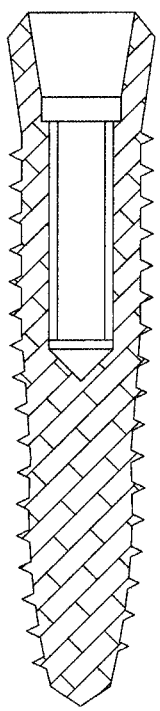
FIG. 6 shows a cross-sectional view of the embodiment of the present invention that is made by being braided as a screw having an internal thread.
Figure 7:
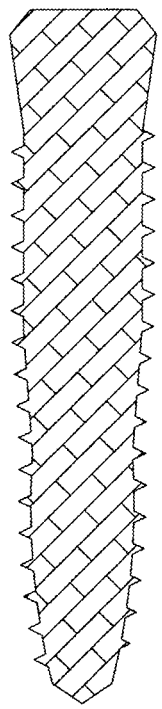
FIG. 7 shows a cross-sectional view of an embodiment of the present invention that is made by being braided as a screw.

Further, the internal layer 10 can be made in the form of a bone screw as shown in FIG. 1 or bone plates (for connection) shown in FIGS. 2-4 or bone screws shown in FIGS. 5-7. These are known configurations of the prior art devices and are examples that can be embodied in the present invention. It is apparent that these types of devices, such as bone screws, bone connection plates/blocks, and tooth root implants, can be made according to the embodiments of the present invention through braiding. Further, braiding can be achieved through various processes. For example, one of the braiding processes is that one of the filaments is taken as a main axis, around which the other filaments are arranged to wrap. An alternative braiding process is that two or three filaments are arranged to inter-entangle and interlacing each other to show a twist form. A further alternative braiding process is that secondary braiding is applied to filaments that have already braided together so that the braided filaments are braided again with other braided or non-braided filaments. These are only illustrative examples of braiding that can be used in the embodiments of the present invention and a variety of other braiding processes that can be used and are not described fully herein are also considered within the scope of "braiding" defined in the present invention.

Figure 9:
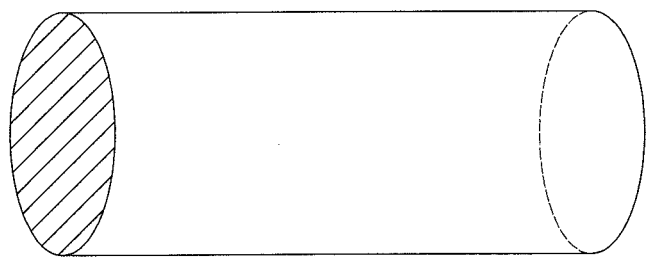
FIG. 9 shows a single fiber filament used in an embodiment of the present invention.
Figure 10:
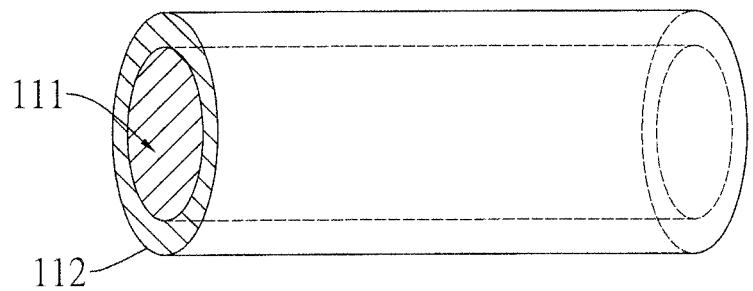
FIG. 10 shows a perspective view of a multilayer fiber filament of an embodiment of the present invention.
Figure 11:
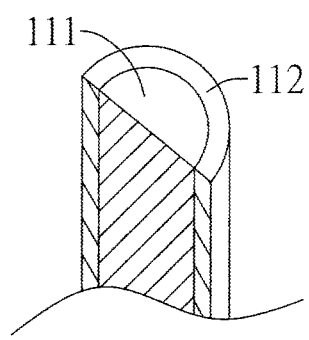
FIG. 11 shows a cross-sectional view of the multilayer fiber filament of the embodiment of the present invention.
Figure 12:
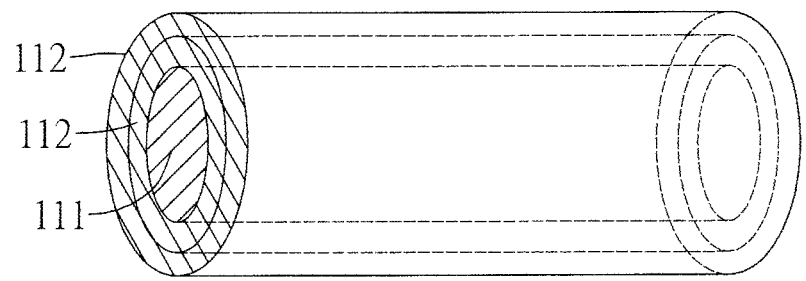
FIG. 12 shows a perspective view of a multilayer fiber filament of an embodiment of the present invention.
Figure 13:
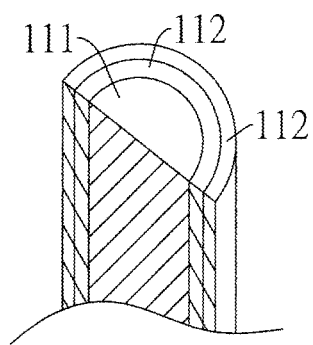
FIG. 13 shows a cross-sectional view of the multilayer fiber filament of the embodiment of the present invention.

Each of the filaments 11 can be formed by drawing a single type of material, as illustrated in a partial perspective view of FIG. 9. Alternatively, the structure shown in FIGS. 10 and 11 can be adopted, which is a multilayer fiber. This type of filament comprises a core layer 111 and a shell layer 112. The core layer 111 is made of an X-ray opacity bioinert material. The shell layer 112 is arranged to enclose a circumferential surface of the core layer 111 and is made of a bioactive glass fiber material, a bioactive ceramic fiber material, HA, or TCP. Alternatively, a filament having two shell layers 112 shown in FIGS. 12 and 13 can also be used. All these described here are examples of filaments that can be used in the present invention. For a bone connection material made of the multilayer structure and material, the shell layer(s) 112 can help bones to grow and can be retained in human body without causing undesired influence, so that there is no need for them to be removed through surgical operations. Further, they are not made of titanium or steel so that they do not cause allergic response of human body. The conventional bone connection material cannot be long retained in human body so that when the patient has healed to quite an extent, a secondary operation must be taken a surgeon on the patient to take out the connection members. This leads to additional risks of anesthesia and postoperative infection caused by the secondary operation. This causes economic, physiologic, and mental burden for the patient. Bioactive glasses are promising scaffold materials for bone regeneration because of their ability to convert to hydroxyapatite (HA), the main mineral constituent of bone, as well as their proven osteoconductivity and their ability to form a strong bone with hard tissues and soft tissues.

The present invention, however, can be designed according to the portion where it is installed and may use a material (such as the multilayer filament described above) that can be long retained in human body, so that there is no need to take the secondary operation and the burden of the patient can be reduced.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

We claim:

1. A bone connection material, comprising:
an internal layer which is formed by braiding a plurality of filaments;
wherein the filaments each comprise:
a core layer, which is made of an X-ray Opacity bioinert material; and
a shell layer, which encloses a circumferential surface of the core layer and is made of hydroxylapatite (HA) or tricalcium phosphate (TCP).

2. The bone connection material according to claim 1, further comprising a covering layer, which encloses the filaments of the internal layer.

3. The bone connection material according to claim 2, wherein the covering layer is made of a thermoplastic resin, a thermosetting resin, or biocompatible polymer.

4. The bone connection material according to claim 3, wherein the covering layer further comprises collagen, hydroxylapatite (HA), or tricalcium phosphate (TCP).

* * * * *